US00PP20955P3

(12) United States Plant Patent
FitzGerald

(10) Patent No.: US PP20,955 P3
(45) Date of Patent: Apr. 27, 2010

(54) ***CAREX* PLANT NAMED 'CARFIT01'**

(50) Latin Name: *Carex oshimensis*
Varietal Denomination: CarFit01

(76) Inventor: Patrick FitzGerald, Oldtown, Stoneyford, Co Kilkenny (IE)

( * ) Notice: Subject to any disclaimer, the term of this patent is extended or adjusted under 35 U.S.C. 154(b) by 0 days.

(21) Appl. No.: 12/291,770

(22) Filed: Nov. 12, 2008

(65) Prior Publication Data

US 2009/0222963 P1 Sep. 3, 2009

(51) Int. Cl.
*A01H 5/00* (2006.01)

(52) U.S. Cl. ..... Plt./384

(58) Field of Classification Search ..... Plt./384
See application file for complete search history.

*Primary Examiner*—Annette H Para

(57) ABSTRACT

A new and distinct *Carex* cultivar named 'CarFit01' is disclosed, characterized by very compact growth, distinctive white variegation on the leaf margins and strong root establishment and development. The new variety is a *Carex*, suitable for commercial production in 15 to 19 inch pots.

1 Drawing Sheet

Figure 1:
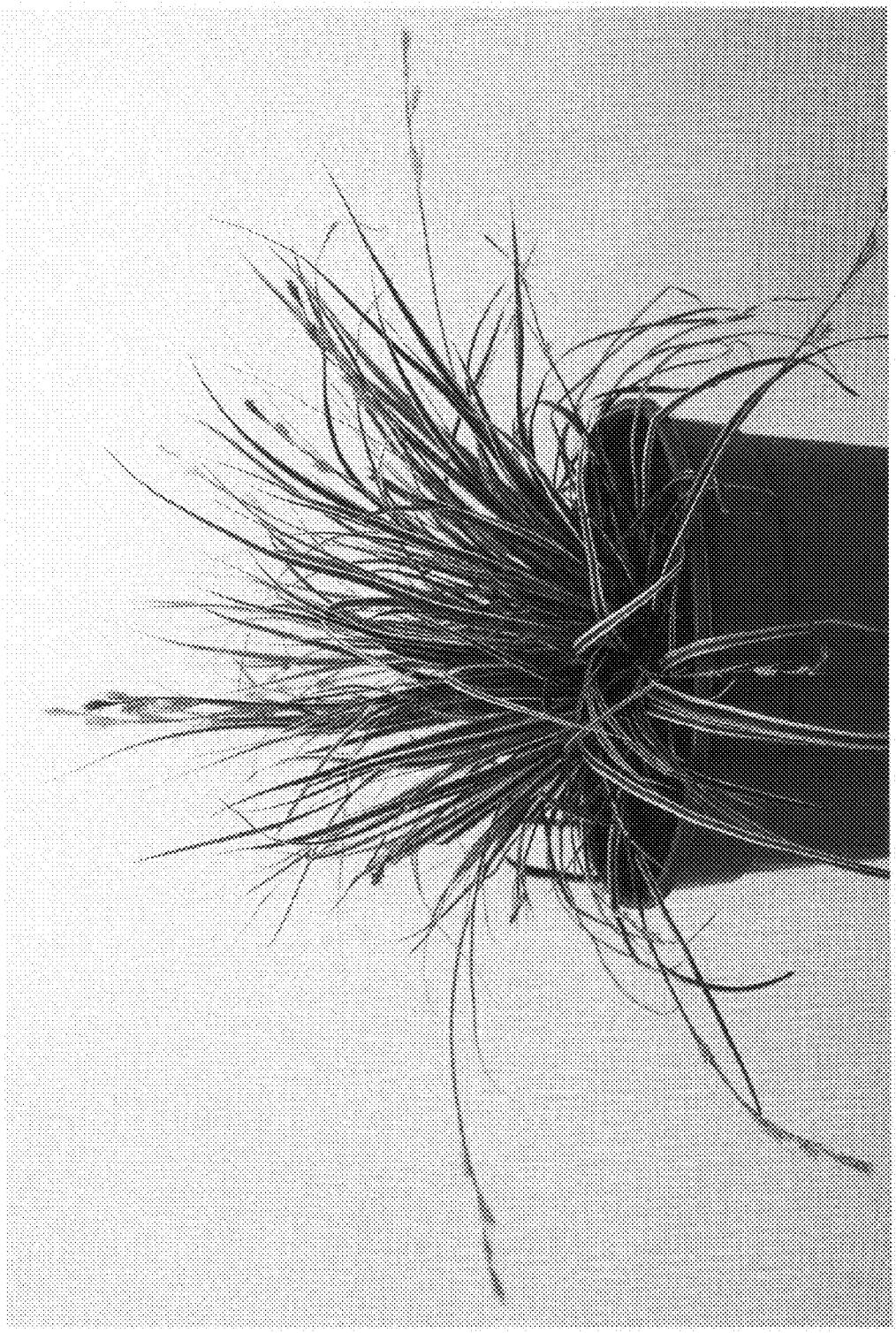

Latin name of the genus and species: *Carex oshimensis*.
Variety denomination: 'CarFit01'.

BACKGROUND OF THE INVENTION

The new cultivar was discovered by the inventor, Patrick FitzGerald, a citizen of the Republic of Ireland in August of 2006 as a naturally occurring, whole plant mutation found in a group of tissue culture plantlets in a commercial laboratory. The parent variety is an unpatented variety, *Carex oshimensis* 'Evergold.'

Asexual reproduction of the new cultivar 'CarFit01' was first performed by tissue culture in Stoneyford, Kilkenny, Ireland in the Summer of 2007 and has shown that the unique features of this cultivar are stable and reproduced true to type on successive generations.

SUMMARY OF THE INVENTION

The cultivar 'CarFit01' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CarFit01' These characteristics in combination distinguish 'CarFit01' as a new and distinct *Carex* cultivar:

1. Compact, easy to grow plants, well suited to landscape uses.
2. Distinctive white variegation on the margins of the leaf.
3. Suitability for commercial production in 15 to 19 cm pots.
4. Strong root establishment and development.

COMPARISON TO PARENT

Plants of the new cultivar 'CarFit01' are similar to plants of the parent variety *Carex oshimensis* 'Evergold' in most horticultural characteristics, however, 'CarFit01' has distinctively different coloration, having white, rather than gold variegation.

COMMERCIAL COMPARISON

'CarFit01' differs from other varieties of *Carix oshimensis* as the only variety with white, rather than gold variegation. 'CarFit01' most closely resembles *Carex conica* 'Snowline,' unpatented, however, 'CarFit01' has longer, wider leaves of a brighter color, and produces a more vigorous plant with better root establishment.

BRIEF DESCRIPTION OF THE PHOTOGRAPH

The accompanying photograph in FIG. 1 illustrates in full color a typical plant of 'CarFit01' grown outdoors, in a 15 cm pot. Age of the plant photographed is 24 weeks. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'CarFit01' plants grown outdoors in Ireland during Spring. Temperatures ranged from 4° C. to 14° C. at night to 13° C. to 27° C. during the day. No artificial light, photoperiodic treatments or chemical treatments were given to the plants. Measurements and numerical values represent averages of typical plant types.

Botanical classification: *Carex oshimensis* 'CarFit01.'

PLANT

Growth habit: Perennial grass, forming clumps.

Plant shape: Flattened globular.

Height: Approximately 25.9 cm.

Plant spread: Approximately 50.6 cm.

Growth rate: Moderate.

Branching characteristics: Herbaceous shoots emerging basally, no lateral branches.
Number of shoots per plant: Approximately 50.
Characteristics of shoots: Triangular shoot bases, typical of *Carex*.
Age of plant described: Approximately 8 months.
Roots: Fine and fibrous.

FOLIAGE

Leaf:
*Arrangement.*—Alternate.
*Compound or single.*—Single
*Quantity of leaves per shoot.*—Average 5.
*Average length.*—Approximately 18 cm.
*Average width.*—Approximately 0.5 cm.
*Shape of blade.*—Linear.
*Aspect.*—Slightly recurved.
*Apex.*—Long acuminate.
*Base.*—Sheathing.
*Margin.*—Smooth, but slightly sharp when rubbed downwards; due to very small, teeth, too small to be visible.
*Texture of top surface.*—Moderately glossy, smooth.
*Texture of bottom surface.*—Smooth, moderately glossy.
*Pubescence.*—None.
*Color.*—Young foliage upper side: Between RHS Green 143A and Yellow-Green 144A. Base Yellow-Green 144C. Tip Green 143A. Leaf margin White 155C. Young foliage under side: Between RHS Green 143A and Yellow-Green 144A. Base Yellow-Green 144C. Tip Green 143A. Leaf margin White 155C. Mature foliage upper side: Near RHS Green; 137A/B. Base Yellow-Green; 144B. Leaf margin White 155A to Green-White 157D. Mature foliage under side: Near RHS Green; 137A/B. Base Yellow-Green; 144B. Leaf margin White 155A to Green-White 157D.
*Venation.*—Type: Parallel. Venation coloration upper side: Indistinguishable from leaf blade. Venation coloration under side: Indistinguishable from leaf blade.

INFLORESCENCE

Flower arrangement: Terminal raceme.
Inflorescence type: Raceme, male and female flowers in separate spikelets.
Inflorescence height: Average 7.5 cm.
Inflorescence width: Average. 0.9 cm.
Quantity of flowers per inflorescence: Average 20 male flowers, placed in an average of 1 spikelet. Average 80 female flowers, placed in an average of 3 spikelets.
Flower type: Typical single *Carex* flower(sedge like.)
Flowering habit: Continuous from April through Summer.
Quantity of flowers per lateral stem: Average 100 flowers per shoot.
Quantity of flower buds per lateral stem: Average 100 flower buds per shoot.
Quantity of flowers and buds per plant: Average 2,400.
Time to flower: Approximately 8 months from planting small rooted division.
Rate of flower opening: After the first flowers open in an inflorescence, all flowers open within 3 weeks.
Fragrance: None.
Flower bud length: Average 0.2 cm.
Flower bud diameter: Average 0.1 cm.
Flower bud shape: Narrow ovate.
Rate of opening: Flower open approximately 3 days after bud stage described.
Flower bud color: Near RHS Yellow-Green 145D.
Flower aspect: Upright.
Flower diameter: Male flowers average 0.4 cm. Female flowers average 0.15 cm.
Flower depth: Average 1 cm, enclosed by 1 glume and a lemma. Female flowers with 1 lemma.
Flower longevity on plant: Approximately 10 days.
Persistence: Persistent.
Petal appearance: Glume and lemma; smooth and matte.
Petal texture: Flume and lemma; smooth. Petal arrangement: Glume at the innerside of each flower, lemma at the outside, opposite the glume.
Petal number: Average 1 glume and 1 lemma.
Petals fused: No.
Petal shape: Glume and lemma lanceolate.
Petal margin: Glume and lemma entire.
Petal tip: Glume; long and narrow acute. Lemma; long mucronate.
Petal length: Glume average 0.8 cm. Lemma average 0.8 cm.
Petal width: Glume; average 0.05 cm. Lemma; average 0.1 cm.
Petal color, when opening, upperside: Glume and lemma of male flowers near RHS Greyed-Orange 165C. Lemma of femal flowers Near RHS Greyed-Orange 164 C/D with a green central vein near RHS Green 143 B/C.
Petal color, when opening, underside: Glume and lemma of male flowers near RHS Greyed-Orange 165C. Lemma of femal flowers Near RHS Greyed-Orange 164 C/D with a green central vein near RHS Green 143 B/C.
Petal color, fully opened, upperside: Glume and lemma of male flowers near RHS Greyed-Orange 165C. Lemma of femal flowers Near RHS Greyed-Orange 164 C/D with a green central vein near RHS Green 143 B/C.
Petal color, fully opened, underside: Glume and lemma of male flowers near RHS Greyed-Orange 165C. Lemma of femal flowers Near RHS Greyed-Orange 164 C/D with a green central vein near RHS Green 143 B/C.
Petal color fading: Not fading.
Petaloids: Not present.
Sepals: No separate sepals visible.
Calyx length: Average 1 cm.
Calyx diameter: Average 0.15 cm.
Peduncle length: Average 23.4 cm.
Peduncle diameter: Average 0.1 cm.
Peduncle angle: Straight, upright from center of shoot. Secondary peduncles, from spikelets nearly straight, an average of 5° angle.
Peduncle strength: Very strong.
Peduncle color: Near RHS Green 137A.
Pedicels: Not present.

REPRODUCTIVE ORGANS

Stamen number: Average 3.
Anther shape: Basifixed.
Anther size: Average 0.2 cm.
Anther color: Near RHS Greyed-Orange 164C/D.
Quantity of pollen: Very low.
Pollen color: Near light Greyed-Orange, however too little quantity to measure with R.H.S. color chart.
Pistil number: Average 3.

Pistil length: Average 0.1 cm.
Stigma shape: Fimbriate.
Stigma color: Near RHS Grey-Brown 199B/C.
Style length: Average 0.02 cm.
Style color: Transparent Grey-Brown, too small to measure with R.H.S. colour chart.
Ovary color: Near RHS Green-White 157A to Greyed-Green 192D.

OTHER CHARACTERISTICS

Disease resistance: Neither resistance nor susceptibility to diseases or pests has been observed in this variety.

Drought tolerance and cold tolerance: Observed to tolerate temperatures to at least 35° C. without any negative effects. Temperature tolerance above this range has not been observed. Tolerance of cold temperatures to −12° C.
Fruit/seed production: Not observed.

What is claimed is:

1. A new and distinct cultivar of *Carex* plant named 'CarFit01' as herein illustrated and described.

* * * * *